United States Patent [19]

Lindner et al.

[11] Patent Number: 4,569,725

[45] Date of Patent: Feb. 11, 1986

[54] SEPARATION OF A $C_4$-HYDROCARBON MIXTURE ESSENTIALLY CONTAINING N-BUTENES AND BUTANES

[75] Inventors: Alfred Lindner, Bobenheim-Roxheim; Klaus Broellos, Seeheim-Jugenheim; Gerhard Sandrock; Klaus Volkamer, both of Frankenthal; Werner Hefner, Lampertheim, all of Fed. Rep. of Germany

[73] Assignee: BASF Aktiengesellschaft, Fed. Rep. of Germany

[21] Appl. No.: 613,388

[22] Filed: May 23, 1984

[30] Foreign Application Priority Data

May 25, 1983 [DE] Fed. Rep. of Germany ....... 3318858

[51] Int. Cl.[4] ............................................. B01D 3/34
[52] U.S. Cl. ........................................ 203/38; 203/29; 203/34; 203/71; 203/DIG. 6; 585/515; 585/864
[58] Field of Search ................ 203/38, 29, 35, 71, 203/80, DIG. 21, DIG. 6, 28, 73, 34; 585/515, 864, 866; 562/600

[56] References Cited

U.S. PATENT DOCUMENTS

| | | | |
|---|---|---|---|
| 3,037,052 | 5/1962 | Bortnick | 585/515 |
| 3,082,271 | 3/1963 | Weitz et al. | 260/677 |
| 3,190,912 | 6/1965 | Robinson | 560/193 |
| 3,285,982 | 11/1966 | Nixon | 585/671 |
| 4,009,203 | 2/1977 | Schmerling | 560/193 |
| 4,232,177 | 11/1980 | Smith, Jr. | 203/28 |
| 4,360,406 | 11/1982 | Ikeda et al. | 203/32 |
| 4,448,643 | 5/1984 | Lindner et al. | 203/DIG. 6 |

FOREIGN PATENT DOCUMENTS 0069014 10/1973 Japan .................................. 562/600

*Primary Examiner*—S. Leon Bashore
*Assistant Examiner*—V. Manoharan
*Attorney, Agent, or Firm*—Keil & Weinkauf

[57] ABSTRACT

A $C_4$-hydrocarbon mixture which essentially contains n-butenes and butanes is separated by a process in which the mixture is reacted with a carboxylic acid in the presence of an acidic catalyst to form a butyl carboxylate, the reaction mixture obtained from the esterification zone is distilled to give, as the top product, a fraction containing the butanes, and, as the bottom product, a fraction containing the resulting butyl carboxylate, the butyl carboxylate is decomposed at elevated temperatures to give the carboxylic acid and n-butenes, and the mixture of n-butenes and carboxylic acid is then distilled, the n-butenes being obtained as the top product, and the carboxylic acid as the bottom product.

8 Claims, No Drawings

SEPARATION OF A C$_4$-HYDROCARBON MIXTURE ESSENTIALLY CONTAINING N-BUTENES AND BUTANES

The present invention relates to a process for the separation of a C$_4$-hydrocarbon mixture, which essentially contains n-butenes and butanes, by reacting the mixture with a carboxylic acid, separating off the butanes from the resulting ester, decomposing the latter at elevated temperatures to give n-butenes and a carboxylic acid, and isolating the n-butenes.

It is known that n-butenes can be separated from butanes by extractive distillation using a selective solvent, eg. furfurol, a distillate containing the butanes, and an extract containing the n-butenes, being obtained. The n-butenes are isolated from the extract in a degassing apparatus, and the degassed solvent is recycled to the extractive distillation. This method employs very expensive apparatus, since the butanes and the n-butenes have very similar boiling points and differ only slightly in their solubilities in the selective solvent, so that very high columns containing, for example, 200 trays are necessary for the extractive distillation.

It is an object of the present invention to provide a process for separating a C$_4$-hydrocarbon mixture essentially containing n-butenes and butanes, which can be carried out using apparatus which is less expensive than that required for the conventional extractive distillation method.

We have found that this and other objects and advantages are achieved, in accordance with the invention, by a process for separating a C$_4$-hydrocarbon mixture which essentially contains n-butenes and butanes, wherein the mixture is reacted with a carboxylic acid in the presence of an acidic catalyst to form a butyl carboxylate, the reaction mixture obtained from the esterification zone is distilled to give, as the top product, a fraction containing the butanes, and, as the bottom product, a fraction containing the resulting butyl carboxylate, the butyl carboxylate is decomposed at elevated temperatures to give the carboxylic acid and n-butenes, and the mixture of n-butenes and carboxylic acid is then distilled, the n-butenes being obtained as the top product, and the carboxylic acid as the bottom product.

Using the novel process, C$_4$-hydrocarbon mixtures containing n-butenes and butanes can be separated into an n-butene fraction and a butane fraction by a cheap distillation method involving simple conventional distillation in a distillation column containing a relatively small number of trays.

C$_4$-Hydrocarbon mixtures which essentially contain n-butenes (ie. 1-butene and/or trans-2-butene and/or cis-2-butene) and butanes (ie. isobutane and/or n-butane) are used as starting materials for the process according to the invention. Advantageously, the content of n-butenes and butanes in the starting C$_4$-hydrocarbon mixture is not less than 90, preferably not less than 94, in particular not less than 98, % by weight. In general, the starting C$_4$-hydrocarbons contain from 1 to 99, preferably not less than 10, in particular not less than 20, % by weight of n-butenes. Starting C$_4$-hydrocarbon mixtures of this type are obtained if, for example, a C$_4$ fraction from an ethylene plant is first subjected to extractive distillation with the aid of a selective solvent to extract butadiene, and isobutylene is then separated off, for example with the production of methyl tert.-butyl ether.

In an esterification stage, the starting C$_4$-hydrocarbon mixture is reacted with a carboxylic acid in the presence of an acidic catalyst to form a butyl carboxylate. Examples of suitable carboxylic acids are aliphatic ones of in general from 1 to 8, preferably from 1 to 6, in particular from 1 to 4, carbon atoms, eg. formic acid, acetic acid, propionic acid, n-butyric acid, isobutyric acid, n-valeric acid, trimethylacetic acid, caproic acid, n-heptanoic acid, caprylic acid or chloroacetic acid. Acetic acid and in particular propionic acid are particularly advantageously used. The carboxylic acids used are, for example, industrial products having the usual purity, for example not less than 95%, preferably not less than 98%, pure.

Examples of suitable acidic catalysts for the esterification are mineral acids, such as sulfuric acid or phosphoric acid, organic sulfonic acids, such as benzenesulfonic acid or p-toluenesulfonic acid, acidic aluminum salts and acidic catalysts of the Friedel-Crafts type, eg. copper(II) chloride or iron(II) chloride, and preferably ion exchangers in the hydrogen form. Examples of suitable ion exchangers are sulfonated coals, sulfonated phenol-formaldehyde resins, sulfonated resins derived from coumarone-indene condensates and in particular sulfonated polystyrene resins, such as crosslinked styrenedivinylbenzene copolymers which are sulfonated in the nucleus. If a liquid or dissolved acidic catalyst is used, it should be employed in general in an amount of about 0.001–0.9, preferably 0.01–0.7, liter per liter of reactor volume. Where solid acidic condensing agents are used, they should be employed in general in an amount of from 0.01 to 1 liter (bulk volume) per liter of reactor volume. The solid acidic condensing agents can be used as such or on a carrier, examples of suitable carrier materials being alumina, silica and active carbon. The esterification can be carried out in, for example, a stirred-kettle or fixed-bed reactor, the latter preferably being used.

For the esterification, the starting C$_4$-hydrocarbon mixture is reacted with the carboxylic acid in the presence of the acidic catalyst, in general at from 40° to 160° C., preferably from 50° to 140° C., in particular from 60° to 120° C. When the acidic catalyst used is an ion exchanger in the hydrogen form, the temperature employed is advantageously from 40° to 150° C., preferably from 50° to 120° C., in particular from 60° to 110° C.

The esterification according to the invention can be carried out under atmospheric pressure, but it is advantageous to use slightly superatmospheric pressure, eg. from 1.01 to 40, in particular from 4 to 30, bar. Depending on the pressure and temperature, the starting C$_4$-hydrocarbon mixture can be used in liquid or gaseous form for the reaction, liquid starting C$_4$-hydrocarbon mixtures being preferably used. The esterification can be carried out batchwise, in which case the reaction time is in general from 1 minute to 5 hours. However, it is preferably carried out continuously, the ratio of the reactor volume in liters to the throughput in liters/h being in general from 0.01 to 5 hours, preferably from 0.3 to 1 hour.

In the esterification, the weight ratio of the carboxylic acid to the n-butenes present in the starting C$_4$-hydrocarbon mixture is in general from 100:1 to 1:2, preferably from 20:1 to 1.1:1, in particular from 4:1 to 1:1. The conversion of the n-butenes is in general from 50 to 90, preferably from 70 to 80, %.

The reaction mixture which is obtained after the esterification, and which as a rule also contains carboxylic acid added in excess for the esterification, is then distilled, the top product being a fraction which contains the butanes and the unconverted n-butenes. If a butane-containing fraction with a very low content of n-butenes is required, it may be advantageous to subject the resulting butane-containing fraction to a further esterification. The conversion of the n-butenes can be increased to 80–95% in this manner.

The bottom product obtained in the distillation of the reaction mixture resulting from the esterification is a fraction which contains the butyl carboxylate formed and may also contain carboxylic acid added in excess for the esterification.

The butyl carboxylate obtained is then decomposed in the second stage of the process at elevated temperatures to give the carboxylic acid and n-butenes. The starting material used for the decomposition can be a butyl carboxylate which is virtually free of carboxylic acid and which has been obtained, for example, by using for the esterification an amount of carboxylic acid which is no more than the stoichiometric amount, or by separating off (for example by distillation) excess carboxylic acid from the bottom product obtained after distillation of the reaction mixture produced in the esterification. Preferably, the butyl carboxylate obtained as a bottom product after the butane fraction has been separated off by distillation is used for the decomposition, without any excess carboxylic acid present being separated off further. However, it is also possible to separate off only some of the excess carboxylic acid.

For the decomposition, the butyl carboxylate is advantageously vaporized, and decomposed at elevated temperatures to give the carboxylic acid and n-butenes. This decomposition can be carried out as a thermal cleavage reaction, ie. as a pyrolysis in the absence of a catalyst. However, it may also be advantageous to carry out the decomposition of the carboxylate in the presence of a catalyst.

In general, acidic catalysts are used, examples of these being ion exchangers in the hydrogen form, such as sulfonated coals, sulfonated phenol-formaldehyde resins, sulfonated resins derived from coumarone-indene condensates, and sulfonated polystyrene resins, such as crosslinked styrene-divinylbenzene copolymers which are sulfonated in the nucleus.

Other advantageous catalyst are solid phosphoric acid catalysts, which contain monophosphoric acid or, preferably, polyphosphoric acid on a solid carrier. Suitable carrier materials for these catalysts are, for example, alumina, silica, active carbon, kieselguhr or pumice, silica gel preferably being used as the carrier.

Other suitable acidic catalysts are acidic metal sulfates, such as sodium bisulfate, calcium bisulfate, aluminum sulfates, nickel sulfate, copper sulfate, cobalt sulfate, cadmium sulfate and strontium sulfate. These acidic metal sulfates can be used as such, but are preferably employed on a carrier. Examples of suitable carrier materials are silica gel, active carbon, alumina and pumice.

In another embodiment of the novel process, the decomposition is carried out using a metal phosphate, in particular a metal hydrogen phosphate, as the acidic catalyst. These phosphates can also contain phosphoric acid in excess of the stoichiometric composition of the acidic metal phosphates, for example in an excess of as much as 65%, preferably as much as 20%, in particular as much as 10%. Examples of metal phosphates of this type which can be used are magnesium phosphates, calcium phosphates, strontium phosphates, barium phosphates, manganese phosphates, nickel phosphates, copper phosphates, cobalt phosphates, cadmium phosphates, iron(II) phosphates, chromium phosphates and, in particular, aluminum phosphates. The metal phosphate catalyst can be used as such or on a carrier, examples of suitable carrier materials being alumina, silica, active carbon and zinc oxide.

The amount of catalyst is in general about 0.01–2, preferably about 0.01–1, kg per kg/hour of butyl carboxylate passing through the reactor. A fixed-bed reactor is preferably used for the decomposition of the butyl carboxylate in the presence of a catalyst.

The decomposition temperature of the butyl carboxylate varies depending on whether the decomposition is carried out in the presence or absence of a catalyst and on the reaction time; where a catalyst is used, it also depends on the type of catalyst. When the thermal decomposition is carried out without a catalyst, the temperatures used are in general from 160° to 500° C., preferably from 170° to 480° C. in particular from 200° to 460° C. When a catalyst is used, the decomposition temperature is in general from 150° to 480° C., preferably from 160° to 400° C., in particular from 180° to 350° C.

The reaction time for the vaporized butyl carboxylate is advantageously from 0.1 to 20, preferably from 1 to 10, seconds. The decomposition of the butyl carboxylate can be carried out under atmospheric pressure, superatmospheric pressure, eg. pressures as high as 30, preferably as high as 20, in particular from 1 to 10, bar, or reduced pressure.

The decomposition of the butyl carboxylate can be carried out batchwise, but is preferably carried out continuously.

The reaction mixture which is obtained in the decomposition, and which contains n-butenes and the carboxylic acid as reaction products, is then distilled, the n-butenes being obtained as the top product, and the carboxylic acid as the bottom product. The carboxylic acid obtained from the separation is advantageously recycled to the esterification zone.

The resulting mixture of n-butenes can be separated into 1-butene and 2-butene by distillation. 1-Butene is an important starting material, for example for the preparation of polymers, such as polybut-1-ene, and for the preparation of butene oxide.

The Example which follows illustrates the invention.

EXAMPLE

The starting $C_4$-hydrocarbon mixture used for the esterification was obtained by first extracting butadiene by extractive distillation from a $C_4$ fraction from an ethylene plant, and then separating off isobutene, with recovery of methyl tert.-butyl ether. The composition of the $C_4$-hydrocarbon mixture after butadiene and isobutene have been separated off was as follows:

1-butene—46% by weight
trans-2-butene—16% by weight
cis-2-butene—11% by weight
isobutene—3% by weight
n-butane—20% by weight
isobutane—4% by weight A mixture of 120 g/hour of this C$_4$-hydrocarbon mixture with 130 g/hour of propionic acid was passed into a stainless steel reactor containing 120 ml of a sulfonated polystyrene-divinylbenzene resin in the hydrogen form (Lewatit SPC 118, size fraction 0.1–1 mm). In the reactor, a reaction temperature of 100° C. and a pressure of 20 bar were maintained. The reaction mixture obtained was fed to a distillation column, a butane mixture being obtained at the top of the column. At the bottom of the distillation column, 200 g/hour of butyl propionate, which also contained 18.5% by weight, based on the bottom product, of excess propionic acid, were taken off and fed into a vaporizer. The vaporized butyl propionate, heated to 190° C., was passed into a tubular cleavage reactor which contained a phosphoric acid/silica gel supported catalyst, and was decomposed at 260° C. to give n-butenes and propionic acid. The reaction product from the ester decomposition was fed into a second distillation column, where 60 g/hour of a mixture of n-butenes having the following composition were obtained as the top product:

1-butene—17.1% by weight
trans-2-butene—37.3% by weight
cis-2-butene—45.5% by weight
butane—0.1% by weight The yield of n-butenes was 66%, based on the n-butenes present in the C$_4$-hydrocarbon mixture used. The bottom product of the second distillation column was propionic acid, which still contained some ester.

When the procedure described above was followed, except that the esterification was carried out in two stages and the propionic acid subsequently recovered in the decomposition stage and still containing butyl propionate was recycled to the esterification, it was possible to increase the yield of n-butenes to above 90%.

We claim:

1. A process for separating a C$_4$-hydrocarbon mixture which contains n-butenes and butanes which comprises
   (a) reacting in an esterification stage the mixture with an aliphatic carboxylic acid of 1 to 8 carbon atoms in the presence of an acidic catalyst at from 40° to 160° C. to form a butyl carboxylate,
   (b) distilling the reaction mixture obtained from esterification stage (a) to give, as the top product, a fraction containing the butanes, and, as the bottom product, a fraction containing the resulting butyl carboxylate,
   (c) decomposing the butyl carboxylate at elevated temperatures to give the carboxylic acid and n-butenes, and
   (d) distilling the mixture of n-butenes and carboxylic acid, to obtain the n-butenes as the top product, and the carboxylic acid as the bottom product.
2. The process of claim 1, wherein the C$_4$-hydrocarbon mixture contains not less than 90% by weight of n-butenes and butanes.
3. The process of claim 1, wherein the carboxylic acid recovered after decomposition of the butyl carboxylate is recycled to the esterification stage.
4. The process of claim 1, wherein the acid used is propionic acid.
5. The process of claim 1, wherein the acidic catalyst used for the esterification is an ion exchanger in the hydrogen form.
6. The process of claim 1, wherein the decomposition of the butyl carboxylate is carried out in the presence of a catalyst.
7. The process of claim 6, wherein the catalyst used for the decomposition is a phosphoric acid/silica gel supported catalyst.
8. The process of claim 1, wherein the decomposition of the butyl carboxylate is carried out at from 200° to 500° C.

* * * * *